United States Patent [19]

Boltralik

[11] Patent Number: 5,420,120
[45] Date of Patent: May 30, 1995

[54] ANTI-INFLAMMATORY GLUCOCORTICOID COMPOUNDS FOR TOPICAL OPHTHALMIC USE

[75] Inventor: John J. Boltralik, Fort Worth, Tex.

[73] Assignee: Alcon Laboratories, Inc., Fort Worth, Tex.

[21] Appl. No.: 169,883

[22] Filed: Dec. 17, 1993

[51] Int. Cl.$^6$ .................... A61K 31/58; C07J 31/00; C07J 43/00; C07J 33/00
[52] U.S. Cl. ..................... 514/172; 514/174; 514/175; 514/176; 540/2; 540/67; 540/108; 540/111; 540/115; 540/116; 540/118; 540/120
[58] Field of Search ............. 514/174, 175, 176, 172; 540/111, 115, 116, 120, 2, 118, 67, 108

[56] References Cited

U.S. PATENT DOCUMENTS

| | | | |
|---|---|---|---|
| 3,007,923 | 11/1961 | Muller et al. | 260/239.55 |
| 3,687,942 | 8/1972 | Anner | 260/239.55 |
| 3,803,133 | 4/1974 | Vogt | 260/239.55 |
| 3,959,260 | 5/1976 | Phillipps et al. | 260/239.5 |
| 4,427,671 | 1/1984 | Torossian et al. | 424/243 |
| 4,472,392 | 9/1984 | Anderson et al. | 424/243 |
| 4,472,393 | 9/1984 | Shapiro | 424/243 |
| 4,477,445 | 10/1984 | Philibert et al. | 424/239 |
| 4,524,134 | 6/1985 | Kominek et al. | 435/61 |
| 4,588,530 | 5/1986 | Lee | 260/397.45 |
| 4,617,299 | 10/1986 | Knepper | 514/178 |
| 4,686,214 | 8/1987 | Boltralik | 514/178 |
| 4,762,919 | 8/1988 | Lee | 540/12 |
| 4,861,765 | 8/1989 | Mitsukuhi et al. | 514/181 |
| 4,913,852 | 4/1990 | Milioni et al. | 514/179 |
| 5,021,408 | 6/1991 | Aubard et al. | 514/179 |
| 5,116,829 | 5/1992 | Hori et al. | 514/172 |
| 5,202,316 | 4/1993 | Claussner et al. | 514/176 |
| 5,215,979 | 6/1993 | Andersson et al. | 514/172 |
| 5,223,493 | 6/1993 | Boltralik | 514/189 |

FOREIGN PATENT DOCUMENTS

| | | |
|---|---|---|
| 936526 | 11/1973 | Canada . |
| 0208202 | 1/1987 | European Pat. Off. . |
| 63303994 | 12/1988 | Japan . |
| 02053794 | 2/1990 | Japan . |
| 04099794 | 3/1992 | Japan . |
| 1302572 | 1/1973 | United Kingdom . |
| 1384994 | 2/1975 | United Kingdom . |
| 1475795 | 6/1977 | United Kingdom . |

OTHER PUBLICATIONS

Carroll, F. I., *J. of Heterocyclic Chemistry*, 5(6), Dec. 1968. pp. 805–811.

Boltralik et al., "In Vivo and in Vitro Hydrolysis of Ophthalmic Steroids Using Rabbit Eyes," *Invest. Ophthal.*, 13 (Supp.):78(1974), abstract.

Eilon et al., "Clinical Evaluation of Clobetasone Butyrate Eye Drops in the Treatment of Anterior Uveitis and its Effect on Intraocular Pressure," *Br. J. Ophthal.*, 65:644–647 (1981).

Dunne et al., "Double-blind Clinical Trial of Topical Steroids in Anterior Uveitis," *Br. J. Ophthal.*, 63:762–767 (1979).

Lloyd–Jones et al., "Clinical evaluation of clobetasone butyrate eye drops in episcleritis," *Br. J. Ophthal.*, 65:641–643 (1981).

Lopez et al., "Dexamethasone 21-($\beta$-Isothiocyanatoethyl) Thioether: A New Affinity Label for Glucocorticoid Receptors," *J. Med. Chem.* 34:1762–1767 (1991).

Lusky et al., "Androstene-17-thioketals," *Arzneim. Forsch/Drug Res.* 36:1787–1795 (1986).

Milioni et al., "Pharmacological Study in vivo of the New Topical Anti-Inflammatory Steroid 21-Thiol-9$\alpha$-fluoro-11$\beta$,17$\alpha$-dihydroxy-16$\alpha$-methyl-3,20--dione-21-acetylamino Cysteine," *Arznelm.Forsch/Drug Res.* 41(11):741–743 (1991).

(List continued on next page.)

*Primary Examiner*—Howard T. Mars
*Assistant Examiner*—Kimberly J. Kestler
*Attorney, Agent, or Firm*—Patrick M. Ryan

[57] ABSTRACT

Topically administrable C-21 thioether glucocorticoid steroid derivatives are disclosed as effective anti-inflammatory agents for the treatment of ophthalmic inflammatory disorders. These C-21 thioether derivatives do not cause a significant increase in intraocular pressure as a side effect.

20 Claims, 1 Drawing Sheet

OTHER PUBLICATIONS

Mitsukuchi et al., "Studies on Topical Antiinflammatory Agents, V. 17-(Alkylthio)- and Methoxyalkanoates of Corticosteroids," *Chem. Pharm. Bull.* 38(3):692–697 (1990).

Mitsukuchi et al., "Studies on Topical Antiinflammatory Agents. III. Synthesis of 17α-Acyloxy-9α-fluoro-11β-hydroxy-16β-methyl-1,4-pregnadiene-3,20-dione 21-Thio Derivatives and Related Compounds," *Chem. Pharm. Bull.* 37(12):3286–3293 (1989).

Philips et al., "Eye Drops of RU 486-6, A Peripheral Steroid Blocker, Lower Intraocular Pressure in Rabbits." *The Lancet,* vol. 1, No. 8380 (1984).

Ramsell et al., "Clinical Evaluation of Clobetasone Butyrate: a comparative study of its effects in postoperative inflammation and on intraocular pressure." *Br. J. Ophthal.* 64:43–45 (1980).

Simons, Jr., et al., "Synthesis and Biological Activity of Some Novel Chemically Reactive Glucocorticoids," *J. Steroid Biochemistry* 13:311–322 (1980).

Simons, Jr., et al., "α-Keto Mesylate: A Reactive, Thiol-Specific Functional Group," *J. Org. Chem.* 45:3084–3088 (1980).

Simons, Jr., et al., "Fluorescent Chemoaffinity Labeling, Potential Application of a New Affinity Labeling Technique to Glucocorticoid Receptors," *Biochemistry* 18(22):4915–4922 (1979).

Southren et al., "Intraocular Hypotensive Effect of a Topically Applied Cortisol Metabolite: 3α, 5β-Tetrahydrocortisol." *Investigative Ophthalmology & Visual Science,* 28:901–903 (1987).

Williamson et al., "Clobetasone Butyrate Eye Drops: Effect on Ocular Inflammation and Intraocular Pressure." *Trans. Ophthal. Soc. U.K.,* 101:27–29 (1981).

Wojnar et al., "Androstene-17-thioketals," *Arzneim-Forsch./Drug Res.* 36(11):1782–1787 (1986).

Mitsukuchi et al., "Studies on Topical Antinflammatory Agents. IV. 21-(Alkylthio)acetates and (Methylthio)-meth-oxides of Corticosteroids," *Chem. Pharm. Bull.* 38(3):786–789 (1990).

FIG. 1

ANTI-INFLAMMATORY GLUCOCORTICOID COMPOUNDS FOR TOPICAL OPHTHALMIC USE

BACKGROUND OF THE INVENTION

1. Field of the Invention

The present invention relates to the topical ophthalmic use of sulfur-containing steroids in the treatment of ophthalmic inflammatory disorders. More particularly, this invention relates to the treatment of ophthalmic inflammatory disorders with C-21 thioether anti-inflammatory steroids which do not cause any significant increase in intraocular pressure as a side effect.

2. Discussion of Related Art

Anti-inflammatory steroids, such as hydrocortisone, prednisolone, dexamethasone, and fluorometholone, are very useful in controlling a wide range of ophthalmic inflammatory conditions. One of the troubling aspects of steroid anti-inflammatory drugs for topical ophthalmic use, however, is the elevation of intraocular pressure (IOP). This side effect precludes the use of these drugs in steroid responders and/or glaucomatous individuals. In either case patients with acute or chronic inflammatory diseases may not be aware of their condition, only to discover it following initiation of treatment. In the first case steroid responders will increase the IOP to dangerous levels or precipitate asteroid glaucoma, both of which will go undetected unless the ophthalmologist examines eye pressure during the treatment course. In the second case and if a chronic inflammatory condition exists, severe damage to the optic nerve can occur leading to blindness. Further discussion of this side effect is presented in an article by Phillips, et al., *The Lancet*, 767–768 (Apr. 7, 1984).

The exact nature and sequence of events leading to IOP elevation by steroids during treatment of acute or chronic inflammatory episodes is unknown. It is established, however, that topical ophthalmic application of glucocorticoid steroids in which the C-21 methylene hydroxy group remains intact and unprotected, such as dexamethasone, will elevate IOP. It is also established that treatment of inflammatory eye disorders with short chain esters (1–5 carbon atoms) at this location do not protect against the IOP side effect due to hydrolysis of the ester back to the primary alcohol (Boltralik, Invest. Ophthalmol. 13: (Supplement): 78 1974). Esterification at C-21 merely increases the partition coefficient of the drug which enhances the amount of drug absorbed/unit dose.

Among other known derivatives of glucocorticoid steroids are C-21 thioesters. British Patent No. 1,475,795, and U.S. Pat. Nos. 3,687,942, 4,427,671, and 5,021,408 teach C-21 thioesters as anti-inflammatory drugs, some of which avoid systemic side effects typically caused by glucocorticoid steroids. British Patent No. 1,475,795 discloses the local treatment of ophthalmological illnesses of an inflammatory and/or allergic nature.

Also among known derivatives of glucocorticoid steroids are C-21 thioethers which are useful as intermediates in making other compounds. U.S. Pat. No. 3,959,260 teaches their use as intermediates in making anaesthetic steroids. U.S. Pat. No. 3,803,133 teaches the use of C-21 thioethers as intermediates in making anti-inflammatory sulfinyl steroids.

Milioni et al., Arzneim-Forsch/Drug Res. 41:741–743 (1991), teach a C-21 thioether derivative, namely 21-thiol-9α-fluoro-11β,17α-dihydroxy-16α-methyl-3,20-dione-21-acetylamino cysteine, as a topical dermatological anti-inflammatory agent lacking systemic side-effects. Mitsukuchi et al., Chem. Pharm. Bull., 37:3286–3293 (1989), teach certain C-21 thio derivatives as topical dermatological anti-inflammatory agents. Neither Milioni et al. nor Mitsukuchi et al. teach ophthalmic use of their respective C-21 derivatives.

The topical dermatological use of C-21 thioethers as anti-inflammatory steroids is also taught in European Patent Application No. 208,202 and U.S. Pat. No. 4,861,765. These references teach C-21 thioethers having reduced systemic side-effects after absorption through the skin.

U.S. Pat. No. 4,913,852 teaches compounds obtained from the associative synthesis of sulfur-containing or sulfur-free amino acids with steroidal derivatives, having glucocorticoid and anti-inflammatory properties. These compounds are taught for various applications, "particularly in the cutaneous and ophthalmic fields." One of the classes of compounds taught by the '852 patent is amino acid-terminated C-21 thioethers. No mention is made of any C-21 thioether not having a terminal amino acid group, nor of any IOP side-effect reduction.

Recent efforts to develop improved steroidal anti-inflammatory drugs for topical ophthalmic use have focused on eliminating the IOP side-effect mentioned above while maintaining anti-inflammatory activity. U.S. Pat. No. 5,223,493 teaches one solution, namely the use of C-21 ether derivatives of dexamethasone. These C-21 ether derivatives retain anti-inflammatory activity and successfully suppress the IOP elevation side effect common to most anti-inflammatory glucocorticoids such as dexamethasone, prednisolone, fluocinolone, etc.

What is needed are additional topically administrable, anti-inflammatory corticosteroids which are useful in treating ophthalmic inflammatory disorders and which do not cause a significant IOP increase as a side-effect.

SUMMARY OF THE INVENTION

The present invention is directed to steroidal C-21 thioether derivatives, ophthalmic pharmaceutical compositions containing the derivatives, and methods of treating ophthalmic inflammatory disorders with these compositions wherein no significant increase in intraocular pressure results.

It is accepted, from studies of structure-activity relationships in steroid chemistry, that seemingly minor structural modifications in asteroid molecule can either significantly enhance, adversely affect, or have no impact on the pharmacological properties of the compound being studied. Any change in pharmacological properties presumably results from a change in the action of the drug at the target cells. Modifications may confer agonistic or antagonistic properties to the steroid molecule. Agonistic drugs are broadly defined as compounds which elicit or activate a biochemical response in situations where the mechanism which elicits the response is undefined. On the other hand, antagonistic drugs are broadly defined as inhibitors of the above-identified selective responses. For example, it has been established that certain side chain modifications stabilize IOP regulation, presumably by depressing or inhibiting the systems responsible for the unwanted IOP side effects. Therefore, if a given steroid is designed to have properties which provide both characteristics of agonism with respect to the retention of anti-inflammatory properties, and antagonism with respect to complete suppression of IOP increase, a true separation of effects is achieved.

The present invention is based on the discovery that certain novel and certain known C-21 thioether derivatives of known anti-inflammatory steroids, such as dexamethasone and flumethasone, confer the desired separation of effects when applied topically to the eye. For example, replacement of the dexamethasone C-21 hydroxyl group with a thioether group results in a compound having the anti-inflammatory properties of dexamethasone, but without elevation of intraocular pressure.

DETAILED DESCRIPTION OF THE INVENTION

The steroidal C-21 thioether derivatives of the present invention have the following structural formula:

wherein:
X = H or halogen;
Y = OH, (=O), $C_1$–$C_5$ O-alkyl or $C_1$–$C_5$ OC(=O)alkyl;
Z = saturated or unsaturated bond;
$R_2$ = H, OH, $C_1$–$C_2$ alkyl, $C_1$–$C_5$ oxalkyl, or $C_1$–$C_5$ oxoalkyl;
$R_3$ = H, OH or $C_1$–$C_3$ alkyl;
$R_2$ & $R_3$ taken together can form wherein A and B are independently H, $C_1$–$C_3$ alkyl, or phenyl, provided however that if either A or B is phenyl, the other is H;
$R_4$ = halogen, H, OH, $C_1$–$C_2$ alkyl, $C_1$–$C_5$ oxalkyl, or $C_1$–$C_5$ oxoalkyl; and
$R_1$ = optionally unsaturated and/or substituted $C_1$–$C_7$ alkyl, branched alkyl, cycloalkyl, carboxyalkyl, hydroxyalkyl, or aralkyl; or optionally substituted aryl; wherein the substituents are halogen, amino, nitro, optionally unsaturated $C_1$–$C_6$ alkyl, aminoalkyl, alkoxy or carboxy;
5-membered heterocyclic ring, optionally benzo-fused, containing at least one C atom and any combination of one or more O and/or N and/or S atoms, optionally unsaturated and/or substituted as above, and wherein the benzo-ring can be substituted as above; or
6-membered heterocyclic ring containing at least two C atoms and any combination of one or more O and/or N atoms, optionally unsaturated and/or substituted as above.

As used herein, 5-membered heterocyclic rings containing at least one C atom and "any combination of one or more O and/or N and/or S atoms" includes 5-membered heterocyclic rings containing: one or more O atoms, such as furanyl; one or more N atoms, such as azolyl, isoazolyl, diazolyl, imidazolyl, triazolyl, or tetrazolyl; one or more S atoms, such as thienyl or dithiolyl; at least one S atom and at least one N atom, such as thiazolyl, isothiazolyl or thiadiazolyl; at least one O atom and at least one N atom, such as oxazolyl, isoxazolyl, oxadiazolyl, oxatriazolyl, or dioxoazolyl; at least one O atom and at least one S atom, such as oxathialyl; and at least one each of O, N and S atoms, such as oxathiazolyl.

Similarly, as used herein "6-membered heterocyclic rings containing at least two C atoms and any combination of one or more O and/or N atoms" includes 6-membered heterocyclic rings containing: one or more O atoms, such as pyranyl and pyronyl; one or more N atoms, such as pyridyl, pyridazinyl, pyrimidinyl or pyrazinyl; and at least one O atom and at least one N atom, such as oxazinyl.

As used herein, "optionally unsaturated and/or substituted" means that the subject group or ring may be 1) saturated and unsubstituted; 2) unsaturated and unsubstituted; 3) saturated and substituted; or 4) unsaturated and substituted.

As used herein, "oxalkyl" means an alkyl group containing an oxygen atom in place of $CH_2$ anywhere in the alkyl chain, including at the point of attachment to the parent (ring) structure, but excluding the terminal position (i.e., OH).

As used herein, "oxoalkyl" means a group containing a carbonyl radical anywhere in an alkyl chain or anywhere in an oxalkyl chain, including carboxy acids and carboxyalkyl groups. For example, oxoalkyl includes the following:

Also included within the scope of the present invention are pharmaceutically acceptable salts and esters of the derivatives of Formula (I).

The preferred classes of compounds of Formula (I) are those in which X, Y, Z, $R_2$, $R_3$, A, B, $R_4$ and $R_1$ are as follows:
X = H, F or Cl; F is more preferred;
Y = OH or $C_1$–$C_5$OC(=O) alkyl; OH is more prefered;
Z = unsaturated bond;

R$_2$=H, OH, or propionate; OH is more preferred;
R$_3$=OH or methyl; methyl is more preferred;
A & B independently=H or methyl
R$_4$=H, F, Cl or methyl; F and methyl are more preferred;
R$_1$=is selected from methyl, ethyl, propyl, isopropyl, butyl, t-butyl, isobutyl, allyl, cyclopropyl, cyclobutyl, cyclopentyl, cyclohexyl, phenyl, benzyl, ω-hydroxyethyl, ω-dihydroxypropyl, carboxymethyl, carboxyethyl, carboxypropyl, carboxybutyl, pyridinyl, thienyl, thiazolyl, imidazolyl, methylimidazolyl, aminothiadiazolyl, methylthiadiazolyl, methyltriazolyl, methyltetrazolyl and benzothiazolyl.

The preferred subclasses of compounds within these preferred classes are:
Subclass 1: X=F; Y=OH; Z=unsaturated bond; R$_2$=OH; R$_3$=CH$_3$; and R$_4$=H.
Especially preferred are:
9-alpha-fluoro-21-(2-hydroxy)ethylthio-19-alpha-methylpregna-1,4-diene-11-beta, 17- alpha-diol-3,20-dione;
9-alpha-fluoro-21-ethylthio-16-alpha-methylpregna-1,4-diene-11-beta, 17-alpha-diol-3,20-dione;
9-alpha-fluoro-21-isopropylthio-16-alpha-methylpregna-1,4-diene-11-beta, 17-alpha-diol-3,20-dione;
9-alpha-fluoro-21-(2-carboxyethyl)thio-16-alpha-methylpregna-1,4-diene, 11-beta, 17-alpha-diol-3,20-dione;
9-alpha-fluoro-21-methylthio-16-alpha-methylpregna-1,4-diene-11-beta, 17-alpha-diol-3,20-dione;
9-alpha-fluoro-21-(2-tert-butylthio)ethylthio-16-alpha-methylpregna-1,4-diene-11-beta, 17-alpha-diol-3,20-dione;
9-Alpha-fluoro-21-allylthio-16-alpha-methylpregna-1,4-diene-11-beta, 17-alpha-diol-3,20-dione;
9-alpha-fluoro-21-(2,3-dihydroxy)propylthio-16-alpha-methylpregna-1,4-diene-11-beta, 17-alpha diol-3,20-dione;
9-alpha-fluoro-21-(2,3-hydroxypropyl)thio-16-alpha-methylpregna-1,4-diene-11-beta-hydroxy-3,20-dione;
9-alpha-fluoro-21-(2-benzothiazolyl)thio-16-alpha-methylpregna-1,4-diene-11-beta, 17-alpha-diol-3,20-dione;
9-alpha-Fluoro-21(5-(1-methyltetrazoyl)thio-16-alpha-methylpregna-1,4-diene-11-beta, 17-alpha-diol-3,20-dione;
9-alpha-fluoro-21(2(5-methyl-1-thia-3,4-diazolyl))thio-16-alpha-methylpregna-1,4-diene-11 beta, 17 alpha-diol-3,20,-dione;
9-alpha-fluoro-21-(2-thiazoline)thio-16-alpha-methylpregna-1,4-diene-11-beta, 17-alpha-diol-3,20-dione;
9-alpha-fluoro-21-(imidazolyl-1-methyl)thio-16-alpha-methylpregna-1,4-diene, 11-beta, 17-alpha-diol-3,20-dione;
9-alpha-fluoro-21-(2-imidazolyl)thio-16-alpha-methylpregna-1,4-diene-11-beta, 17-alpha-diol-3,20-dione;
9-alpha-fluoro-21-(3-(4-methyl-1,2,4-triazolyl))thio-16-alpha-methylpregna-1,4-diene-11-beta, 17-alpha-diol-3,20-dione;
9-alpha-fluoro-21-(2-thienyl)thio-16-alpha-methylpregna-1,4-diene-11-beta, 17-alpha-diol-3,20-dione;
9-alpha-fluoro-21-(2-pyridinyl)thio-16-alpha-methylpregna-1,4-diene-11-beta, 17-alpha-diol-3,20-dione;
9-alpha-fluoro-21-(2-(5-amino-1-thia-3,4-diazolyl))thio-16-alpha-methylpregna-1,4-diene-11-beta, 17-alphadiol-3,20-dione; and
9-alpha-fluoro-21-benzylthio-16-alpha-methylpregna-1,4-diene, 11-beta, 17-alpha-3,20-dione.

Subclass 2: X=F; Y=OH; Z=unsaturated bond; R$_2$=OH; R$_3$=CH$_3$; and R$_4$=F.
Especially preferred are:
6,9-alpha-difluoro-21-propylthio-16-alpha-methylpregna-1,4-diene-11-beta, 17-diol-3,20-dione;
6,9-alpha-difluoro-21-allylthio-16-alpha-methylpregna-1,4-diene-11-beta, 17-alpha-diol-3,20-dione;
6,9-alpha-difluoro-21-(2-hydroxypropyl)thio-16-alpha-methylpregna-1,4-diene-11-beta, 17-alpha-diol-3,20-dione;
6,9-alpha-difluoro-21-(carbethoxymethyl)thio-16-alpha-methylpregna-1,4-diene-11-beta, 17-alpha-diol-3,20-dione;
6,9-alpha-difluoro-21-(2-carboxyethyl)thio-16-alpha-methylpregna-1,4-diene-11-beta, 17-alpha-diol-3,20-dione;
6,9-alpha-difluoro-21-methylthio-16-alpha-methylpregna-1,4-diene-11-beta, 17-alpha-diol-3,20-dione;
6,9-alpha-difluoro-21-(2-(5-methyl-1-thia-3,4-diazolyl))thio-16-alpha-methylpregna-1,4-diene-11-beta, 17-alpha-diol-3,20-dione; and
6,9-alpha-difluoro-21-(2-thiazolyl)thio-16-alpha-methylpregna-1,4-diene-11-beta, 17-alpha-diol-3,20-dione.

Subclass 3: X=F; Y=OH; Z=unsaturated bond; R$_4$=H; and R$_2$ and R$_3$ taken together form wherein A and B are independently H or CH$_3$.
Especially preferred is:
9-alpha-fluoro-21-propylthio-16,17-alpha-isopropylidine-11-beta-hydroxy-1,4-diene-3,20-dione.

Subclass 4: X=F; Y=OH; Z=unsaturated bond; R$_2$=propionate; R$_3$=CH$_3$; and R$_4$=H. Especially preferred is:
9-alpha-fluoro-21-ethylthio-16-alpha-methylpregna-1,4-diene-11-beta, 17-alpha-propionoxy-3,20-dione.

The novel C-21 thioether derivatives of the present invention are those of Formula (I) wherein:
R$_1$=5-membered heterocyclic ring, optionally benzo-fused, containing at least one C atom and any combination of one or more O and/or N and/or S atoms, optionally unsaturated and/or substituted as above, and wherein the benzo-ring can be substituted as above; or
6-membered heterocyclic ring containing at least two C atoms and any combination of one or more O and/or N atoms, optionally unsaturated and/or substituted as above.

The C-21 thioether derivatives of Formula (I) can be prepared by a variety of known synthetic procedures. For example, the C-21 thioether derivatives of Formula (I) can be prepared by reacting known steroids, such as dexamethasone, desoxymetasone, flumethasone or triamcinolone acetonide, with tosyl or mesyl chlorides. Alternatively, C-21 bromo or iodo derivatives of the aforementioned steroids may be reacted with metallic alkyl, alkene, alkyne, heterocyclic or condensed heterocyclic thiolates under neutral conditions or mercaptans under basic conditions. Reaction temperatures can vary from −10° to 0° C. for most straight chain or branched alkyl mercaptans, but are generally room temperature for straight chain, branched alkyl, hetero or condensed heterocyclic metallic thiolates. Reaction temperatures range from 40° to 78° C. for heterocyclic mercaptans. In some instances the use of metallic lithium, potassium or sodium thiolates, (sodium is preferred) in place of mercaptans can reduce the number of side products with hetero- or condensed heterocyclic reactants. Yet another method of synthesis is that taught in U.S. Pat. No. 4,861,765, the entire contents of which are hereby incorporated by reference in the present specification.

The above-described methods of synthesis are further illustrated in the following examples:

EXAMPLE 1

9-alpha-fluoro-21-(2-hydroxy)ethylthio-19-alpha-methylpregna-1,4-diene-11-beta, 17-alpha-diol-3,20-dione Dexamethasone mesylate 0.85 g (1.81 mMol.) was dissolved in 25 ml dry acetone in a 100 mL 3-necked flask fitted with a serum cap, an Argon inlet and magnetic stirrer. Eight equivalents (Eq) of triethylamine was added and the temperature reduced to −10 degrees. Thioethanol 8 Eq was added via a canulla over 5 minutes and the reaction allowed to proceed over 2 hrs at −5° to 0° C. The reaction contents were transferred to a separatory funnel containing 200 ml acidulated water (pH 1) and 200 ml ethyl acetate. The organic phase was washed successively with 1×200 mL water, 1×200 ml 1% sodium hydroxide and 4×200 mL water and brine. The organic phase was dried with magnesium sulfate, decolorized with activated carbon filtered through a small celite bed and evaporated to dryness. The product was crystallized from acetone/hexane yielding 0.53 g (65) % yield; M.P. 210°–211° C. Calculated for C24H33FO5S C=63.69%, H=7.35%, S=7.09%; Found C= 63.75%, H=7.35%, S=7.13%. CI/MS, M/z=452.

H-NMR (DMSOd6): 0.78(d, J=7.2, 3H, C16 CH3); 0.87(s, 3H, C18 CH3); 1.49(s, 3H, C19 CH3); 4.78(t, J=5.58, 1H, S—C—C—OH); 5.06(s, 1H, 17 alpha OH) 3.67(AB, J=16.92, Δν=75, 2H, C21 CH2); 5.3(m,1H, 11 beta OH); 6.0(s,1H, H4); 6.2(dd, J=10.14, 1H, H2); 7.3(d, J=10.14, 1H, H1).

Coupling constants are reported in Hz.

In a manner similar to Example 1 above, Examples 2–15 were prepared under argon or nitrogen, using dry acetone as solvent with bases such as triethylamine or 1,5-diazabicyclo[4.3.0]non-5 ene (DBN). Thiol reagents were added via canulla or in bulk, ranging in concentration from 1–10 mol equivalents. Reaction temperatures ranged from −10° to 0° to 2° C. or room temperature (mercaptides) with completion times of 0.5 to 4 hours. Compounds were isolated generally by extraction into ethyl acetate, washed with acid/base/water to neutrality or precipitated with ice water, filtered, dissolved in ethyl acetate, washed with water, dried with magnesium sulfate, evaporated to dryness and crystallized directly or the compound was isolated by column chromatography on silica gel. All examples were characterized by H-NMR, CI/MS and elemental analysis.

2=9-alpha-fluoro-21-ethylthio-16-alpha methylpregna-1,4-diene-11-beta, 17-alpha-diol-3,20-dione.

3=9-alpha-fluoro-21-isopropylthio-16-alpha-methyl-pregna-1,4-diene-11-beta, 17-alpha-diol-3,20-dione.

4=6,9-alpha-difluoro-21-propylthio-16-alpha-methyl-pregna-1,4-diene-11-beta, 17-diol-3,20-dione.

5=9-alpha-fluoro-21-ethylthio-16-alpha-methylpregna-1,4-diene-11-beta, 17-alpha-propionoxy-3,20-dione.

6=9-alpha-fluoro-21-(2-carboxyethyl)thio-16-alpha-methylpregna-1,4-diene, 11-beta, 17-alpha-diol-3,20-dione.

7=9-alpha-fluoro-21-methylthio-16-alpha-methylpregna-1,4-diene-11-beta, 17-alpha-diol-3,20-dione.

8=9-alpha-fluoro-21-(2-tert-butylthio)ethylthio-16-alpha-methylpregna-1,4-diene-11-beta, 17-alpha-diol-3,20-dione.

9=9-alpha-fluoro-21-allylthio-16-alpha-methylpregna-1,4-diene-11-beta, 17-alpha-diol-3,20-dione.

10=9-alpha-fluoro-21-(2,3-dihydroxy)propylthio-16-alpha-methylpregna-1.4-diene-11-beta, 17-alpha diol-3,20-dione.

11=6,9-alpha-difluoro-21-allylthio-16-alpha-methyl-pregna-1,4-diene-11-beta, 17-alpha-diol-3,20-dione.

12=6,9-alpha-difluoro-21-(2-hydroxypropyl)thio-16-alpha-methylpregna-1,4-diene-11-beta, 17-alpha-diol-3,20-dione.

13=6,9-alpha-difluoro-21-(carbethoxymethyl)thio-16-alpha-methylpregna-1,4-diene-11-beta, 17-alpha-diol-3,20-dione.

14=9-alpha-fluoro-21-(2,3-hydroxypropyl)thio-16-alpha-methylpregna-1,4-diene-11-beta, 17-alpha-diol-3,20-dione.

15=6,9-alpha-difluoro-21-(2-carboxyethyl)thio-16-alpha-methylpregna-1,4-diene-11-beta, 17-alpha-diol-3,20-dione.

EXAMPLE 16

9-alpha-fluoro-21-(2-benzothiazolyl)thio-16-alpha-methylpregna-1,4-diene-11-beta, 17-alpha-diol-3,20-dione Sodium hydride, 0.1 g (80%), (1.28 Eq) was de-oiled 2× with 5 mL pentane in a 100 mL 3-necked flask fitted with an Argon inlet and magnetic stirrer. The de-oiled hydride was dried with Argon, 5 mL dry tetrahydrofuran (THF) added, followed by dropwise addition of 2 Eq of 2-Mercaptobenzothiazole in 5 mL dry THF from a self leveling drop funnel over 6 minutes. Hydrogen evolution stopped after 20 minutes and the reaction stirred for 1.5 hrs. The reaction was filtered to remove a slight precipitate and the yellow solution evaporated to dryness. The residue was dissolved in chloroform and precipitated with hexane. The precipitate was dissolved in acetone and evaporated at high vacuum to give 0.45 g (88%) yield of the thiazole salt. The salt was dissolved in 7 mL acetone and combined with 0.6 of dexamethasone methane sulphonate (1.28 mMol) in 9 mL dry acetone and stirred 5 minutes after which time a gel formed which was broken by the additional 4 mL acetone. The reaction was allowed to proceed an additional 1.5 hrs at room temperature after which time the reaction was complete. The product was purified by silica gel chromatography using acetone/CHCl3 1/15 and recrystallized from acetone/isopropyl ether to yield 0.52 g of a flaky white powder. M.P. 209°–211° C. decomp. Calculated for C29H32FO4 NS2; C=64.30%, H=5.95%, N=2.59%, S=11.84%; Found C=64.41%, H=5.96%, N=2.61%, S=11.76%. CI/MS M/z=541. H-NMR(DMSOd6) 7.95(dd, J=1.34, 2H, =CH—C=C—CH=), 7.4(m, 2H, —CH=CH—)

Example 16 above and Examples 17 and 18 were prepared similarly under argon or nitrogen using acetone or DMF or acetone and DMF as co-solvent. Either the sodium mercaptide using NaH was prepared in-situ or obtained from commercial sources, the concentration of which ranged from 2–8 mol equivalents.

Reactions were complete after 1.5 hrs at room temperature. Products were dissolved in ethyl acetate, washed with water, dried with magnesium acetate and crystallized as such or isolated by column chromatography on silica gel. All compounds were characterized by H-NMR, CI/MS and elemental analysis.

17=6,9-alpha-difluoro-21-methylthio-16-alpha-methylpregna-1,4-diene-11-beta, 17-alpha-diol-3,20-dione.

18=9-alpha-fluoro-21-(5-(1-methyltetrazoyl))thio-16-alpha-methylpregna-1,4-diene-11-beta, 17-alpha-diol-3,20-dione.

EXAMPLE 19

9-alpha-fluoro-21-(2-(5-methyl-1-thia-3,4-diazolyl))thio-16-alpha-methylpregna-1,4-diene-11-beta, 17-alpha-diol-3,20-dione Dexamethasone tosylate 0.8 g (1.46 mMol) in 10 mL dry dimethylformamide in a 100 mL 3-necked flask fitted with a condenser, nitrogen inlet and magnetic stirrer was heated to 67°–70° C. in an oil bath. Two Eq of 2-Mercapto-5-methyl-1,3,4-thiadiazole and 5 Eq of triethylamine was added and heated for 15 minutes in which time the reaction was complete. The reaction was cooled to 25° C. and 50 mL ice-water added to produce a voluminous precipitate. An additional 15 mL water was added and the solid stirred for 0.5 hr, filtered and air dried. The residue was dissolved in 200 mL ethyl acetate, washed with 25 mL water, brine and dried with MgSO4 and evaporated to dryness to produce a glass/crystalline mixture. The mixture was dissolved in hot ethyl acetate (80° C.) and evaporated to 40–50 mL, 2 volumes of hexane added and evaporation continued until crystallization started. Crystallization was completed overnight at 0°–2° C. to furnish 0.46 g (65.2%) yield. M.P. 221°–222° C. Calculated for $C_{25}H_{31}FO_4N_2S_2$ C=59.23%, H=6.17%, N=5.53%, S=12.65%; Found C=59.23%, H=6.19%, N=5.48%, S=12.66%; CI/MS M/z=506; H-NMR(DMSOd6) 2.68 (s, 3H, S—C=N).

Example 19 above and Examples 20–30 were prepared in a similar manner under argon or nitrogen, using either acetone or DMF as a solvent or acetone and DMF as a co-solvent, and bases such as triethyl amine or diisopropylethylamine (DIEA) or DIEA in combination with solid KOH. Thiol reagents were added by canulla or solid addition or dissolved in a suitable solvent and added by drop funnel in concentrations ranging from 1–5 mole quivalents. Reaction temperatures ranged from 45°–80° C. with completion times of 0.25 to 1.5 hrs. In some instances with acetone solvent overnight reflux or heating to 50° C. with DMF was required for reaction completion. Compounds were isolated by extraction into ethyl acetate, washed with acid/base/water to neutrality, dried with magnesium sulfate, evaporated to dryness and crystallized directly or isolated by column chromatography on silica gel. All examples were characterized by H-NMR, CI/MS and elemental analysis.

20=9-alpha-fluoro-21-(2-thiazoline)thio-16-alpha-methylpregna-1,4-diene-11-beta, 17-alpha-diol-3,20-dione.

21=9-alpha-fluoro-21-(imidazolyl-1-methyl)thio-16-alpha-methylpregna-1,4-diene, 11-beta, 17-alpha-diol-3,20-dione.

22=9-alpha-fluoro-21-(2-imidazolyl)thio-16-alpha-methylpregna-1,4-diene-11-beta, 17-alpha-diol-3,20-dione.

23=9-alpha-fluoro-21-(3-(4-methyl-1,2,4-triazolyl))thio-16-alpha-methylpregna-1,4-diene-11-beta, 17-alpha-diol-3,20-dione.

24=9-alpha-fluoro-21-(2-thienyl)thio-16-alpha-methylpregna-1,4-diene-11-beta, 17-alpha-diol-3,20-dione.

25=6,9-alpha-difluoro-21-(2-(5-methyl-1-thia-3,4-diazolyl))thio-16-alpha-methylpregna-1,4-diene-11-beta, 17-alpha-diol-3,20-dione.

26=9-alpha-fluoro-21-propylthio-16-alpha, 17-alpha-isopropylidine-11-beta-hydroxy-1,4-diene-3,20-dione.

27=6,9-alpha-difluoro-21-(2-thiazolyl)thio-16-alpha-methylpregna-1,4-diene-11-beta, 17-alpha-diol-3,20-dione.

28=9-alpha-fluoro-21-(2-pyridinyl)thio-16-alpha-methylpregna-1,4-diene-11-beta, 17-alpha-diol-3,20-dione.

29=9-alpha-fluoro-21-(2-(5-amino-1-thia-3,4-diazolyl))thio-16-alpha-methylpregna-1,4-diene-3,20-dione.

30=9-alpha-fluoro-21-benzylthio-16-alpha-methylpregna-1,4-diene, 11-beta, 17-alpha-3,20-dione.

The anti-inflammatory activity of the thioether derivatives of the present invention was demonstrated in three model systems. Table 1 shows the results from the Carrageenan Foot Edema Assay, Winter et al, Proc. Soc. Exp. Biol. Med., 111:544 (1962), which evaluates the anti-inflammatory potency and drug stability following oral dosing.

TABLE 1

| CARRAGEENAN INDUCED PAW EDEMA | | | |
|---|---|---|---|
| Compound (Example No.) | Dose (mg/kg) | % Change | Standard Dexamethasone (1 mg/kg) |
| 2 | 10.0 | −77* | −70* |
|   | 1.0 | −57* | −86* |
|   | 0.1 | −9 | −86* |
| 4 | 10.0 | −82 | −70 |
|   | 1.0 | −86*/72* | −86*/80*(0.3 mg/kg) |
|   | 0.1 | −57*/63* | −85*/−80*(0.3 mg/kg) |
|   | 0.01 | −32* | −80*/−80*(0.3 mg/kg) |
|   | 0.001 | −9 | −80/−80*(0.3 mg/kg) |
| 6 | 10.0 | −66* | −70* |
|   | 1.0 | −65* | −75* |
|   | 0.1 | −7 | −75* |
| 7 | 10.0 | −71* | −70* |
|   | 1.0 | −67* | −75* |
|   | 0.1 | −25* | −70* |
| 9 | 10.0 | −83* | −79* |
|   | 1.0 | −75* | −75* |
|   | 0.1 | −16 | −86* |
| 10 | 10.0 | −67* | −70* |
|   | 1.0 | −60* | −75* |
|   | .01 | −11 | −86* |
| 11 | 0.1 | −73* | −92* |
|   | 0.01 | −12 | −60 (0.1 mg/kg) |
| 12 | 0.1 | −67* | −92* |
|   | 0.01 | −4 | −60* (0.1 mg/kg) |
| 16 | 1.0 | −24* | −65 |
|   | 0.1 | −25* | " |
|   | 0.01 | −9 | " |
| 17 | 0.1 | −63* | −92* |
|   | 0.01 | −21 | −60* (0.1 mg/kg) |
| 19 | 10.0 | −81* | −80* |
|   | 1.0 | −72* | −80 (0.3 mg/kg) |
|   | 0.1 | −38* | −80 (0.3 mg/kg) |
|   | 0.3 | −36* | −80 (0.3 mg/kg) |
|   | 0.001 | −10 | −80 (0.3 mg/kg) |
| 20 | 10.0 | −77* | −79* |
|   | 1.0 | −77* | −75* |
|   | 0.1 | −20 | −86* |
| 22 | 10.0 | −73* | −79* |
|   | 1.0 | −79* | −75* |
|   | 0.1 | −16 | −86* |
| 28 | 0.1 | −43* | −92* |

*Significant at the 95% level

The anti-inflammatory potency following transcorneal penetration of the drug into the inflamed uveal tract was evaluated using the Endotoxin Induced Uveitis Assay described by Williams et al., Curr. Eye Res., 2:465 (1983). The results are shown in Table 2.

TABLE 2

| Endotoxin Induced Uveitis | | | |
|---|---|---|---|
| Compound | Dose % | % Change | Standard Dexamethasone 0.1% |
| 4 | 1.0 | −53* | −43* |
|  | 0.5 | +10 | −43* |
|  | 0.1 | −20/−8 | −62*/−43* |
| 14 | 0.1 | −26* | −57* |
| 19 | 0.1 | −9 | −61* |
| 25 | 1.0 | −87* | −81* |
|  | 0.1 | −34 | −60* |

*Significant at the 95% level

The anti-inflammatory potency following corneal inflammation was evaluated in the Clove Oil Keratitis Assay described by Leibowitz et al., Arch. Ophthalmol., 92:427 (1974). The results are shown in Table 3.

TABLE 3

| Clove Oil Keratitis | | | |
|---|---|---|---|
| Compound | Dose % | % Change | Standard Dexamethasone 0.1% |
| 4 | 1.0 | −56* | −46* |
|  | 0.1 | −24* | −46* |
| 9 | 1.0 | −11 | PA = −38[a] |
| 19 | 1.0 | −47* | −48* |
|  | 0.1 | −34* | −48* |
| 22 | 1.0 | −23* | PA = −38[a] |

*significant at 95% level
[a] = 1% Preunisolone Acetate standard

Figure 1:
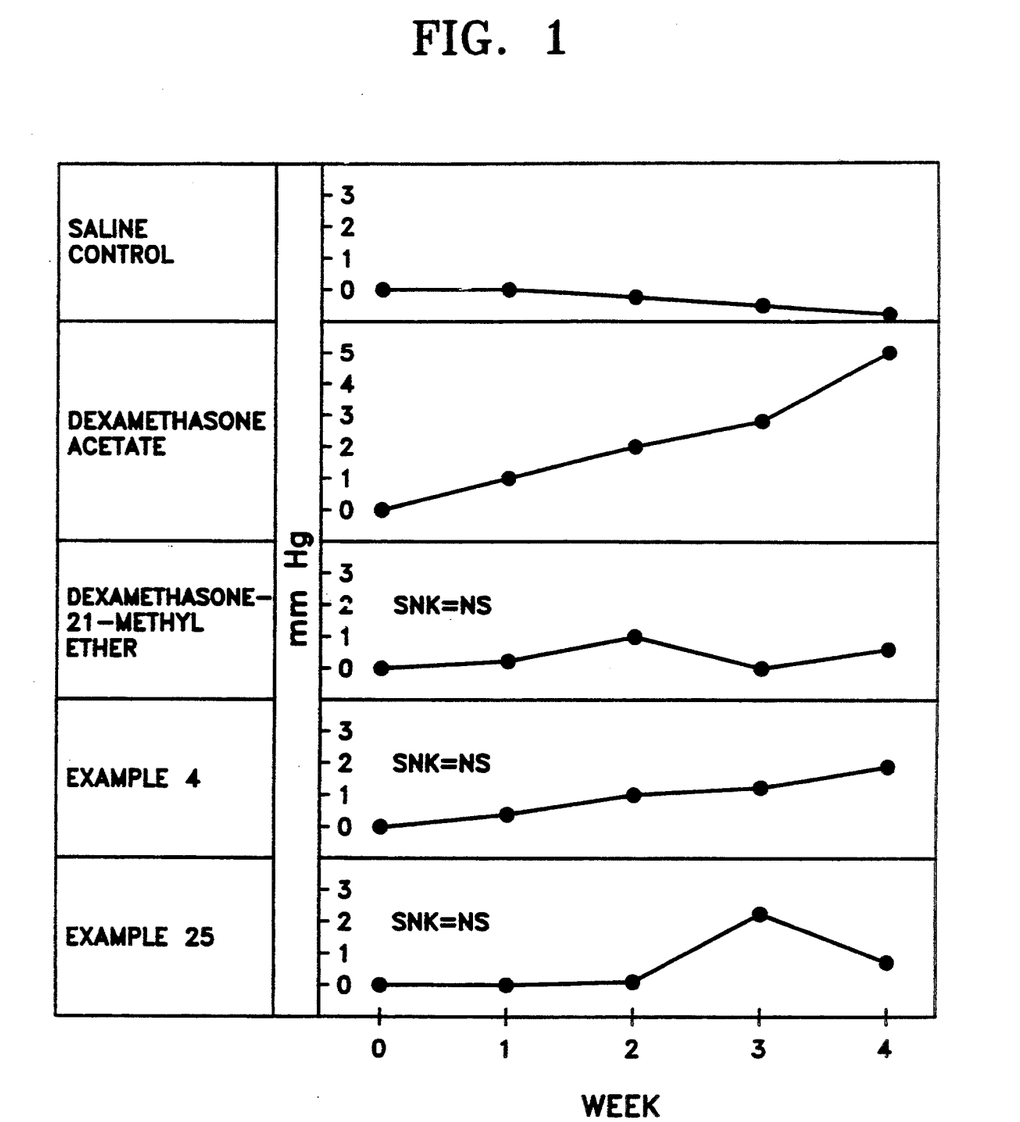
FIG. 1 shows the IOP stabilization properties of certain C-21 modified glucocorticoid steroid ethers in New Zealand White Rabbits.

The lack of an adverse effect on IOP with the compounds of the present invention was demonstrated in a rabbit model, U.S. Pat. Nos. 4,617,299 and 4,812,448, and the results are shown in FIG. 1. Both a least-significant difference and a Student-Newman-Keuls statistical comparison using dexamethasone-21-methyl ether (U.S. Pat. No. 5,223,493) as control showed no significant increase in IOP elevation for the Examples shown.

The steroidal C-21 thioether derivatives of Formula (I) may be incorporated into various types of ophthalmic pharmaceutical compositions for delivery to the eye, such as solutions, suspensions, gels and ointments. Formulations containing one or more drug compounds of this invention may also contain ophthalmologically acceptable preservatives, surfactants, viscosity enhancers, buffers, tonicity agents, etc. For example, one or more of the compounds of Formula (I) may be combined with a preservative, surfactant, viscosity enhancer, buffer, sodium chloride and water to form an aqueous, sterile ophthalmic suspension.

In order to prepare sterile ophthalmic ointment formulations, one or more of the drug compounds is combined with a preservative in a hydrophilic/hydrophobic base such as mineral oil, liquid lanolin, or white petrolatum. Sterile ophthalmic gel formulations may be prepared by suspending the active ingredient in a hydrophilic base prepared from the combination of Carbopol-940 (a carboxyvinyl polymer available from the B. F. Goodrich Company), sodium hydroxide, sodium chloride, and preservatives. The specific type of formulation selected will depend on various factors, such as the type of inflammation being treated (e.g., internal or external) and dosage frequency. Ophthalmic suspensions, ointments, and gels are the preferred dosage forms.

The steroid derivatives of Formula (I) will normally be contained in these formulations in an amount in the range of about 0.05% to about 2.0% by weight, preferably about 0.5 to about 1.0% by weight.

The formulations described in the following example further illustrate the dosage forms which may be utilized in the present invention.

EXAMPLE 31

In the following formulations, the term "steroid" represents one or more of any of the above-described C-21 thioether derivatives of Formula (I).

| Ingredient | Composition (wt. %) |
|---|---|
| Suspension | |
| Steroid | .05–2.0 |
| Benzalkonium Chloride | 0.001–0.02 |
| Polysorbate-80 or Tyloxopol | 0.01–1.0 |
| Phosphate Buffer pH | 5–100 mMol |
| Sodium Chloride | 0–0.9 |
| Hydroxypropyl methyl cellulose | 0.1–0.5 |
| Water | q.s. |
| Ointment | |
| Steroid | 0.05–2.0 |
| Chlorobutanol | 0.5 |
| Methyl or propyl parabens | 0.01–0.1 |
| Mineral Oil | 0–10 |
| Liquid Lanolin | 0–10 |
| White petrolatum | q.s. |
| Gel | |
| Steroid | 0.05–2.0 |
| Carbopol-940 | 1–4 |
| Sodium Hydroxide | (q.s.) (pH: 4.5–8.0) |
| Sodium Chloride | 0–0.9 |
| Water | q.s. |

The treatment method of the present invention comprises applying an ophthalmic pharmaceutical composition containing an anti-inflammatory effective amount of one or more steroid derivatives of Formula (I) to the affected ocular tissue when indicated for the relief of inflammation.

Examples of ophthalmic inflammatory disorders which can be treated by the compositions of the present invention include, but are not limited to: acute or chronic conjunctivitis; acute or chronic anterior segmental uveitis in normal individuals, steroid responders, and individuals with frank primary open and/or closed angle glaucoma; inflammation and IOP elevation resulting from intraocular lens implantation and/or inflammation; and IOP elevation following trabecular filtering or laser surgeries. The dosage regimen utilized will depend on various factors, such as the severity of the inflammation and the duration of action of the particular formulation utilized. In general, the above-described formulations may be topically applied, for example, as drops to the upper globe, or as a 0.5–1.0 cm strip of ointment or gel to the lower conjunctival sac of the eye. At the physician's discretion, suspensions will generally be applied two to four times daily, while ointments or gels will generally be applied once or twice daily. The application of sustained release formulations (e.g., polymer based gels) once daily at bedtime will be preferred for some conditions.

The above-described formulations are useful in treating virtually any type of ocular inflammation. These formulations are especially useful in the treatment of ocular inflammation in patients who are predisposed to experiencing elevated intraocular pressure when treated with a conventional steroid compound; this class of patients, which is estimated as constituting approximately 5% of the general population, is referred to as "steroid responders." The formulations also have special value in treating ocular inflammation in patients suffering from open angle glaucoma, since it has been estimated that approximately 92% of these patients experience a large increase in intraocular pressure after chronic (e.g., 2 to 6 weeks) steroid therapy. The formulations also find special use in treating the inflamed ocular tissue of patients who are predisposed to open-angle glaucoma or ocular hypertension.

I claim:

1. A C-21 thioether corticosteroid derivative having the following formula:

wherein:

X = H or halogen;

Y = OH, (=O), $C_1-C_5$ O-alkyl or $C_1-C_5$ OC(=O)alkyl;

Z = saturated or unsaturated bond;

$R_2$ = H, OH, $C_1-C_2$ alkyl, $C_1-C_5$ oxalkyl, or $C_1-C_5$ oxoalkyl;

$R_3$ = H, OH or $C_1-C_3$ alkyl;

$R_2$ & $R_3$ taken together can form wherein A and B are independently H, $C_1-C_3$ alkyl, or phenyl, provided however that if either A or B is phenyl, the other is H;

$R_4$ = halogen, H, OH, $C_1-C_2$ alkyl, $C_1-C_5$ oxalkyl, or $C_1-C_5$ oxoalkyl; and $R_1$ = 5-membered heterocyclic ring, optionally benzo-fused, containing at least one C atom and any combination of one or more O and/or N and/or S atoms, optionally unsaturated and/or substituted as above, and wherein the benzo-ring can be substituted as above; or 6-membered heterocyclic ring containing at least two C atoms and any combination of one or more O and/or N atoms, optionally unsaturated and/or substituted as above; and pharmaceutically acceptable salts and esters thereof.

2. The C-21 thioether corticosteroid derivative of claim 1 wherein the derivative is selected from the group consisting of:

9-alpha-fluoro-21-(2-benzothiazolyl)thio-16-alpha-methylpregna-1,4-diene-11-beta, 17-alpha-diol-3,20-dione;

9-alpha-fluoro-21-(5-(1-methyltetrazoyl))thio-16-alpha-methylpregna-1,4-diene-11-beta, 17-alpha-diol-3,20-dione;

9-alpha-fluoro-21-(2-(5-methyl-1-thia-3,4-diazolyl))thio-16-alpha-methylpregna-1,4-diene-11-beta, 17-alpha-diol-3,20-dione;

9-alpha-fluoro-21-(2-thiazoline)thio-16-alpha-methylpregna-1,4-diene-11-beta, 17-alpha-diol-3,20-dione;

9-alpha-fluoro-21-(imidazolyl-1-methyl)thio-16-alpha-methylpregna-1,4-diene, 11-beta, 17-alpha-diol-3,20-dione;

9-alpha-fluoro-21-(2-imidazolyl)thio-16-alpha-methylpregna-1,4-diene-11-beta, 17-alpha-diol-3,20-dione;

9-alpha-fluoro-21-(3-(4-methyl-1,2,4-triazolyl))thio-16-alpha-methylpregna-1,4-diene-11-beta, 17-alpha-diol-3,20-dione;

9-alpha-fluoro-21-(2-thienyl)thio-16-alpha-methylpregna-1,4-diene-11-beta, 17-alpha-diol-3,20-dione;

6,9-alpha-difluoro-21-(2-(5-methyl-1-thia-3,4-diazolyl))thio-16-alpha-methylpregna-1,4-diene-11-beta, 17-alpha-diol-3,20-dione;

6,9-alpha-difluoro-21-(2-thiazolyl)thio-16-alpha-methylpregna-1,4-diene-11-beta, 17-alpha-diol-3,20-dione;

9-alpha-fluoro-21-(2-pyridinyl)thio-16-alpha-methylpregna-1,4-diene-11-beta, 17-alpha-diol-3,20-dione; and 9-alpha-fluoro-21-(2-(5-amino-1-thia-3,4-diazolyl))thio-16-alpha-methylpregna-1,4-diene-3,20-dione.

3. A topically administrable, ophthalmic pharmaceutical composition for treating ophthalmic inflammation, which comprises an anti-inflammatory effective amount of a C-21 thioether corticosteroid derivative of the formula:

wherein:

X = H or halogen;

Y = OH, (=O), $C_1-C_5$ O-alkyl or $C_1-C_5$ OC(=O)alkyl;

Z = saturated or unsaturated bond;

$R_2$ = H, OH, $C_1-C_2$ alkyl, $C_1-C_5$ oxalkyl, or $C_1-C_5$ oxoalkyl;

$R_3$ = H, OH or $C_1-C_3$ alkyl;

$R_2$ & $R_3$ taken together can form wherein A and B are independently H, $C_1-C_3$ alkyl, or phenyl, provided however that if either A or B is phenyl, the other is H;

$R_4$ = halogen, H, OH, $C_1-C_2$ alkyl, $C_1-C_5$ oxalkyl, or $C_1-C_5$ oxoalkyl; and $R_1$ = optionally unsaturated and/or substituted $C_1-C_7$ alkyl, branched alkyl, cycloalkyl, carboxyalkyl, hydroxyalkyl, or aralkyl; or optionally substituted aryl; wherein the substituents are halogen, amino, nitro, optionally unsaturated $C_1$-$C_6$ alkyl, aminoalkyl, alkoxy or carboxy;

5-membered heterocyclic ring, optionally benzofused, containing at least one C atom and any combination of one or more O and/or N and/or S atoms, optionally unsaturated and/or substituted as above, and wherein the benzo-ring can be substituted as above; or 6-membered heterocyclic ring containing at least two C atoms and any combination of one or more O and/or N atoms, optionally unsaturated and/or substituted as above; and pharmaceutically acceptable salts and esters thereof.

4. The composition of claim 3 wherein the C-21 thioether corticosteroid derivative has X=H, F or Cl;
Y=OH or $C_1$-$C_5$ OC(=O) alkyl;
Z=unsaturated bond;
$R_2$=H, OH, or propionate;
$R_3$=OH or methyl;
A & B independently=H or methyl
$R_4$=H, F, Cl or methyl;
$R_1$=is selected from methyl, ethyl, propyl, isopropyl, butyl, t-butyl, isobutyl, allyl, cyclopropyl, cyclobutyl, cyclopentyl, cyclohexyl, phenyl, benzyl, ω-hydroxyethyl, ω-dihydroxypropyl, carboxymethyl, carboxyethyl, carboxypropyl, carboxybutyl, pyridinyl, thienyl, thiazolyl, imidazolyl, methylimidazolyl, aminothiadiazolyl, methylthiadiazolyl, methyltriazolyl, methyltetrazolyl and benzothiazolyl.

5. The composition of claim 4 wherein the C-21 thioether corticosteroid derivative has X=F
Y=OH
Z=unsaturated bond;
$R_2$=OH
$R_3$=methyl
A & B independently=H or methyl
$R_4$=F or methyl
$R_1$=is selected from methyl, ethyl, propyl, isopropyl, butyl, t-butyl, isobutyl, allyl, cyclopropyl, cyclobutyl, cyclopentyl, cyclohexyl, phenyl, benzyl, ω-hydroxyethyl, ω-dihydroxypropyl, carboxymethyl, carboxyethyl, carboxypropyl, carboxybutyl, pyridinyl, thienyl, thiazolyl, imidazolyl, methylimidazolyl, aminothiadiazolyl, methylthiadiazolyl, methyltriazolyl, methyltetrazolyl and benzothiazolyl.

6. The composition of claim 4 wherein the C-21 thioether corticosteroid derivative has X=F; Y=OH; Z=unsaturated bond; $R_2$=OH; $R_3$=$CH_3$; and $R_4$=H.

7. The composition of claim 6 wherein the C-21 thioether corticosteroid derivative is selected from the group consisting of:

9-alpha-fluoro-21-(2-hydroxy)ethylthio-19-alpha-methylpregna-1,4-diene-11-beta, 17-alpha-diol-3,20-dione;

9-alpha-fluoro-21-ethylthio-16-alpha-methylpregna-1,4-diene-11-beta, 17-alpha-diol-3,20-dione;

9-alpha-fluoro-21-isopropylthio-16-alpha-methyl-pregna-1,4-diene-11-beta, 17-alpha-diol-3,20-dione;

9-alpha-fluoro-21-(2-carboxyethyl)thio-16-alpha-methylpregna-1,4-diene, 11-beta, 17-alpha-diol-3,20-dione;

9-alpha-fluoro-21-methylthio-16-alpha-methylpregna-1,4-diene-11-beta, 17-alpha-diol-3,20-dione;

9-alpha-fluoro-21-(2-tert-butylthio)ethylthio-16-alpha-methylpregna-1,4-diene-11-beta, 17-alpha-diol-3,20-dione;

9-Alpha-fluoro-21-allylthio-16-alpha-methylpregna-1,4-diene-11-beta, 17-alpha-diol-3,20-dione;

9-alpha-fluoro-21-(2,3-dihydroxy)propylthio-16-alpha-methylpregna-1.4-diene-11-beta, 17-alpha diol-3,20-dione;

9-alpha-fluoro-21-(2,3-hydroxypropyl)thio-16-alpha-methylpregna-1,4-diene-11-beta-hydroxy-3,20-dione;

9-alpha-fluoro-21-(2-benzothiazolyl)thio-16-alpha-methylpregna-1,4-diene-11-beta, 17-alpha-diol-3,20-dione;

9-alpha-fluoro-21-(5-(1-methyltetrazoyl)thio-16-alpha-methylpregna-1,4-diene- 11-beta, 17-alpha-diol-3,20-dione;

9-alpha-fluoro-21-(2(5-methyl-1-thia-3,4-diazolyl))thio-16-alpha-methylpregna-1,4-diene-11 beta, 17 alpha-diol-3,20,-dione;

9-alpha-fluoro-21-(2-thiazoline)thio-16-alpha-methylpregna-1,4-diene-11-beta, 17-alpha-diol-3,20-dione;

9-alpha-fluoro-21-(imidazolyl-1-methyl)thio-16-alpha-methylpregna-1,4-diene, 11-beta, 17-alpha-diol-3,20-dione;

9-alpha-fluoro-21-(2-imidazolyl)thio-16-alpha-methylpregna-1,4-diene-11-beta, 17-alpha-diol-3,20-dione;

9-alpha-fluoro-21-(3-(4-methyl-1,2,4-triazolyl))thio-16-alpha-methylpregna-1,4-diene-11-beta, 17-alpha-diol-3,20-dione;

9-alpha-fluoro-21-(2-thienyl)thio-16-alpha-methylpregna-1,4-diene-11-beta, 17-alpha-diol-3,20-dione;

9-alpha-fluoro-21-(2-pyridinyl)thio-16-alpha-methylpregna-1,4-diene-11-beta, 17-alpha-diol-3,20-dione;

9-alpha-fluoro-21-(2-(5-amino-1-thia-3,4-diazolyl))thio-16-alpha-methylpregna-1,4-diene-11-beta, 17-alphadiol-3,20-dione; and 9-alpha-fluoro-21-benzylthio-16-alpha-methylpregna-1,4-diene, 11-beta, 17-alpha-3,20-dione.

8. The composition of claim 4 wherein the C-21 thioether corticosteroid derivative has X=F; Y=OH; Z=unsaturated bond; $R_2$=OH; $R_3$=$CH_3$; and $R_4$=F.

9. The composition of claim 8 wherein the C-21 thioether corticosteroid derivative is selected from the group consisting of:

6,9-alpha-difluoro-21-propylthio-16-alpha-methylpregna-1,4-diene-11-beta, 17-diol-3,20-dione;

6,9-alpha-difluoro-21-allylthio-16-alpha-methylpregna-1,4-diene-11-beta, 17-alpha-diol-3,20-dione;

6,9-alpha-difluoro-21-(2-hydroxypropyl)thio-16-alpha-methylpregna-1,4-diene-11-beta, 17-alpha-diol-3,20-dione;

6,9-alpha-difluoro-21-(carbethoxymethyl)thio-16-alpha-methylpregna-1,4-diene-11-beta, 17-alpha-diol-3,20-dione;

6,9-alpha-difluoro-21-(2-carboxyethyl)thio-16-alpha-methylpregna-1,4-diene-11-beta, 17-alpha-diol-3,20-dione;

6,9-alpha-difluoro-21-methylthio-16-alpha-methyl-pregna-1,4-diene-11-beta, 17-alpha-diol-3,20-dione;

6,9-alpha-difluoro-21-(2-(5-methyl-1-thia-3,4-diazolyl))thio-16-alpha-methylpregna-1,4-diene-11-beta, 17-alpha-diol-3,20-dione; and 6,9-alpha-difluoro-21-(2-thiazolyl)thio-16-alpha-methylpregna-1,4-diene-11-beta, 17-alpha-diol-3,20-dione.

10. The composition of claim 4 wherein the C-21 thioether corticosteroid derivative has X=F; Y=OH; Z=unsaturated bond; R$_4$=H; and R$_2$ and R$_3$ taken together form wherein A and B are independently H or CH$_3$.

11. The composition of claim 10 wherein the C-21 thioether corticosteroid derivative is 9-alpha-fluoro-21-propylthio-16,17-alpha-isopropylidine-11-beta, hydroxy-1,4-diene-3,20-dione.

12. The composition of claim 4 wherein the C-21 thioether corticosteroid derivative has X=F; Y=OH; Z=unsaturated bond; R$_2$=propionate; R$_3$=CH$_3$; and R$_4$=H.

13. The composition of claim 12 wherein the C-21 thioether corticosteroid derivative is 9-alpha-fluoro-21-ethylthio-16-alpha-methylpregna-1,4-diene-11-beta, 17-alpha-propionoxy-3,20-dione.

14. The composition of claim 3 wherein the amount of C-21 thioether corticosteroid is from about 0.05 to about 2.0% by weight.

15. The composition of claim 14 wherein the amount of the C-21 thioether corticosteroid is from about 0.5 to about 1.0% by weight.

16. A method of treating ophthalmic inflammatory disorders which comprises topically administering to the affected eye an anti-inflammatory effective amount of a C-21 thioether corticosteroid derivative of the formula:

wherein:
X=H or halogen;
Y=OH, (=O), C$_1$-C$_5$ O-alkyl or C$_1$-C$_5$ OC(=O)alkyl;
Z=saturated or unsaturated bond;
R$_2$=H, OH, C$_1$-C$_2$ alkyl, C$_1$-C$_5$ oxalkyl, or C$_1$-C$_5$ oxoalkyl;
R$_3$=H, OH or C$_1$-C$_3$ alkyl;
R$_2$ & R$_3$ taken together can form wherein A and B are independently H, C$_1$-C$_3$ alkyl, or phenyl, provided however that if either A or B is phenyl, the other is H;

R$_4$=halogen, H, OH, C$_1$-C$_2$ alkyl, C$_1$-C$_5$ oxalkyl, or C$_1$-C$_5$ oxoalkyl; and R$_1$ optionally unsaturated and/or substituted C$_1$-C$_7$ alkyl, branched alkyl, cycloalkyl, carboxyalkyl, hydroxyalkyl, or aralkyl; or optionally substituted aryl; wherein the substituents are halogen, amino, nitro, optionally unsaturated C$_1$-C$_6$ alkyl, aminoalkyl, alkoxy or carboxy;

5-membered heterocyclic ring, optionally benzo-fused, containing at least one C atom and any combination of one or more O and/or N and/or S atoms, optionally unsaturated and/or substituted as above, and wherein the benzo-ring can be substituted as above; or 6-membered heterocyclic ring containing at least two C atoms and any combination of one or more O and/or N atoms, optionally unsaturated and/or substituted as above; and pharmaceutically acceptable salts and esters thereof.

17. The method of claim 16 wherein the C-21 thioether corticosteroid derivative has
X=H, F or Cl;
Y=OH or C$_1$-C$_5$ OC(=O) alkyl;
Z=unsaturated bond;
R$_2$=H, OH, or propionate;
R$_3$=OH or methyl;
A & B independently=H or methyl
R$_4$=H, F, Cl or methyl;
R$_1$=is selected from methyl, ethyl, propyl, isopropyl, butyl, t-butyl, isobutyl, allyl, cyclopropyl, cyclobutyl, cyclopentyl, cyclohexyl, phenyl, benzyl, ω-hydroxyethyl, ω-dihydroxypropyl, carboxymethyl, carboxyethyl, carboxypropyl, carboxybutyl, pyridinyl, thienyl, thiazolyl, imidazolyl, methylimidazolyl, aminothiadiazolyl, methylthiadiazolyl, methyltriazolyl, methyltetrazolyl and benzothiazolyl.

18. The method of claim 17 wherein the C-21 thioether corticosteroid derivative has
Y=OH
X=F
Z=unsaturated bond;
R$_2$=OH
R$_3$=methyl
A & B independently=H or methyl
R$_4$=F or methyl
R$_1$=is selected from methyl, ethyl, propyl, isopropyl, butyl, t-butyl, isobutyl, allyl, cyclopropyl, cyclobutyl, cyclopentyl, cyclohexyl, phenyl, benzyl, ω-hydroxyethyl, ω-dihydroxypropyl, carboxymethyl, carboxyethyl, carboxypropyl, carboxybutyl, pyridinyl, thienyl, thiazolyl, imidazolyl, methylimidazolyl, aminothiadiazolyl, methylthiadiazolyl, methyltriazolyl, methyltetrazolyl and benzothiazolyl.

19. The method of claim 16 wherein the amount of C-21 thioether corticosteroid is from about 0.05 to about 2.0% by weight.

20. The method of claim 19 wherein the amount of the C-21 thioether corticosteroid is from about 0.5 to about 1.0% by weight.

* * * * *

UNITED STATES PATENT AND TRADEMARK OFFICE
CERTIFICATE OF CORRECTION

PATENT NO. : 5,420,120
DATED : May 30, 1995
INVENTOR(S) : Boltralik

It is certified that error appears in the above-indentified patent and that said Letters Patent is hereby corrected as shown below:

Col. 1, line 27: "asteroid" should read -- a steroid --.

Col. 2, line 50: "asteroid" should read -- a steroid --.

Col. 8, line 48: "0.6" should read -- 0.6 g --.

Col. 9, line 3: "magnesium acetate" should read -- magnesium sulfate --.

Col. 11, Table 3, footnote a: "Preunisolone" should read -- Prednisolone --.

Signed and Sealed this

Twenty-sixth Day of September, 1995

Attest:

BRUCE LEHMAN

Attesting Officer    Commissioner of Patents and Trademarks